United States Patent [19]

Goldberg et al.

[11] Patent Number: 4,564,594

[45] Date of Patent: Jan. 14, 1986

[54] FERMENTATION PROCESS FOR PRODUCTION OF CARBOXYLIC ACIDS

[75] Inventors: Israel Goldberg, Jerusalem, Israel; Barry Stieglitz, Overbrook Hills, Pa.

[73] Assignee: E. I. Du Pont de Nemours and Company, Wilmington, Del.

[21] Appl. No.: 509,701

[22] Filed: Jun. 30, 1983

[51] Int. Cl.$^4$ .......................... C12P 7/56; C12P 7/40; C12P 7/44; C12P 7/48; C12P 7/46; C12P 1/02; C12P 1/845; C12P 1/38

[52] U.S. Cl. ..................... 435/139; 435/136; 435/142; 435/143; 435/144; 435/145; 435/171; 435/244; 435/254; 435/110; 435/112; 435/939

[58] Field of Search ............. 435/136, 139, 142, 143, 435/144, 145, 171, 939, 244, 254, 110, 112

[56] References Cited

U.S. PATENT DOCUMENTS

| | | | |
|---|---|---|---|
| 2,326,986 | 8/1943 | Waksman | 435/145 |
| 2,327,191 | 8/1943 | Kane et al. | 435/145 |
| 2,861,922 | 11/1958 | Lubowitz et al. | 435/145 |
| 2,912,363 | 11/1959 | La Roe | 435/145 |
| 3,293,145 | 12/1966 | Leavitt et al. | 435/244 |
| 3,372,094 | 3/1968 | Gold et al. | 435/144 |
| 3,511,752 | 5/1970 | Tanaka et al. | 435/110 |
| 3,795,585 | 3/1974 | Suzuki et al. | 435/244 |
| 4,212,942 | 7/1980 | Miyazaki et al. | 435/244 |
| 4,370,159 | 1/1983 | Holtz | 435/254 |

FOREIGN PATENT DOCUMENTS

| | | | |
|---|---|---|---|
| 0636199 | 2/1962 | Canada | 435/112 |
| 0064484 | 5/1977 | Japan | 435/244 |
| 679087 | 2/1951 | United Kingdom | 435/145 |
| 700316 | 2/1951 | United Kingdom | 435/145 |

OTHER PUBLICATIONS

Rhodes et al., *Appl. Microbiol.,* 7:74–80 (1959).
Rhodes et al., *Appl. Microbiol.,* 10:9–15 (1962).
Takinami et al., *Agr. Biol. Chem.,* 27:858–863 (1963).
Takinami et al., *Agr. Biol. Chem.,* 28:114–119 (1964).
Takinami et al., *Agr. Biol. Chem.,* 29:351–359 (1965).
Trumpy et al., *J. Gen. Microbiol.,* 30:381–393 (1963).
Millis et al., *J. Gen. Microbiol.,* 30:365–379 (1963).

*Primary Examiner*—Thomas G. Wiseman
*Assistant Examiner*—Robin Teskin
*Attorney, Agent, or Firm*—Scott G. Hallquist

[57] ABSTRACT

An improved fermentation process for producing carboxylic acids, especially fumaric acid, is disclosed. The improvement comprises growing fungi of genus Rhizopus in the presence of an effective amount of at least one additive selected from the group consisting of fatty acid esters having fatty acid residues of 12 to 24 carbons, and triglyceride mixtures.

12 Claims, No Drawings

FERMENTATION PROCESS FOR PRODUCTION OF CARBOXYLIC ACIDS

BACKGROUND OF THE INVENTION

This invention relates to a fermentation process for producing certain carboxylic acids. More particularly, the invention concerns a method of improving the rate of production of certain carboxylic acids in Rhizopus cultures by use of selected growth media additives.

Production of certain carboxylic acids, e.g., fumaric acid, by fungi of the genus Rhizopus has been a subject of several patents and other contributions to the technical literature. Rhodes et al., *Appl. Microbiol.* 7:74–80 (1959), describe a series of fermentation experiments in which optimal conditions were sought for maximizing fumaric acid yields in *Rhizopus arrhizus* cultures. In a later publication, *Appl. Microbiol.* 10:9–15 (1962), Rhodes et al. describe preferred conditions for producing fumaric acid by fermentation of *Rhizopus arrhizus* in 20 liter fermentors. In particular, use of a polypropylene glycol to control foaming, and $CaCO_3$ to continuously neutralize the resulting fumaric acid, are disclosed.

Waksman, U.S. Pat. No. 2,326,986, describe a method for producing fumaric acid by fermentation of *Rhizopus nigricans*, or other fungi of the order Mucorales, in the presence of zinc and iron salts. Kane, et al., U.S. Pat. No. 2,327,191, disclose a process for producing fumaric acid by submerged aerobic fermentation of *Rhizopus nigricans*. Lubowitz, et al., U.S. Pat. No. 2,861,922, disclose use of nickel salts to promote fumaric acid production by Rhizopus fungi. La Roe, U.S. Pat. No. 2,912,363, describes improvements in fumaric acid yields by Rhizopus and related fungi which are attributable to limiting the concentration of nitrogen sources in culture media.

A number of patents or publications disclose that fats, fatty acids, or their derivatives can be added to microbial fermentation media as supplemental carbon sources, or as yield promoters in fermentation processes for producing glutamic acid and certain antibiotics. For example, U.K. Pat. Nos. 679,087 and 700,316 disclose use of fats or fatty acids as carbon sources or supplements.

A series of papers by Takinami et al., *Agr. Biol. Chem.* 27:858–863 (1963); 28:114–119 (1964); and 29:351–359 (1965); disclose methods of promoting L-glutamic acid yields in *Brevibacterium lactofermentum* fermentations by addition of fatty acid esters and other fatty acid derivatives, e.g., polyoxyethylene sorbitan monostearate. Trumpy, et al., *J. Gen. Microbiol.* 30:381–393 (1963) and Millis, et al., *J. Gen. Microbiol.* 30:365–379 (1963) report improved yields of citric acid in cultures of *Aspergillus niger* to which oils with a high content of unsaturated fatty acids, e.g., peanut oil, were added.

Fermentation processes, especially those employing inexpensive and abundant carbon sources derived from biomass, offer alternative sources of supply of commercially important organic acids. Such organic acids include fumaric acid, which is utilized by the plastics industry in the manufacture of polyester and alkyd resins; lactic and malic acids, which are utilized by the food industry; and succinic acid, which is consumed in the manufacture of pharmaceuticals, plastics, and protective coatings. Thus, improved fermentation processes for producing these compounds are desirable.

SUMMARY OF THE INVENTION

The present invention provides an improvement in a fermentation process for producing carboxylic acids selected from the group consisting of fumaric acid, succinic acid, malic acid, lactic acid, and mixtures thereof, the improvement comprising growing fungi of genus Rhizopus in the presence of at least one culture medium additive selected from the group consisting of (1) fatty acid esters having fatty acid residues of 12 to 24 carbons, and (2) triglyceride mixtures, wherein the culture medium additive is present at a concentration effective to increase production of said carboxylic acids.

DETAILED DESCRIPTION OF THE INVENTION

The present invention provides an improved process for producing fumaric acid, succinic acid, lactic acid, malic acid or mixtures of these carboxylic acids by growth of fungi of the genus Rhizopus. The invention is characterized by a process improvement comprising addition of fatty acid esters, or mixtures thereof, to the culture media in which the fungi are grown. Rates of production of these carboxylic acids, particularly fumaric acid, are enhanced when Rhizopus cultures are grown in the presence of fatty acid esters. The increased rates of carboxylic acid production observed using the process of the invention are believed to be attributable to incorporation of fatty acids into fungi cytoplasmic membranes, resulting in alteration of membrane permeability and rapid excretion of fumaric acid and other metabolites into the extracellular environment.

Microorganisms

Suitable fungal species for the process of the invention are fungi of the genus Rhizopus. Examples of suitable species include *Rhizopus arrhizus*, *R. oryzae*, and *R. nigricans*. Because of observed higher productivity, *R. arrhizus* is a preferred species. *R. arrhizus* NRRL 1526, a strain described by Rhodes, et al., *Appl. Microbiol.* 7:74–80 (1959), is a particularly preferred microorganism for the process of the present invention.

Culture Media

Various media formulations known to be suitable for Rhizopus fermentation can be employed in the process of the invention. Generally, a suitable medium will provide a carbon source, a nitrogen source, inorganic salts and one or more of the fatty acid ester or triglyceride additives which characterize the invention.

Suitable carbon sources include glucose, sucrose, xylose, fructose, invert sugar, maltose, invert high test molasses, syrups, and various starches, grains, malted grains, cereal products or other materials containing any of the foregoing substances. Glucose is a preferred source. When glucose is employed as a carbon source, it is preferred to use from about 10 to about 16 g glucose per 100 mL of medium.

Suitable nitrogen sources include such organic and inorganic sources as urea, ammonium chloride, ammonium sulfate, ammonium acetate, ammonium nitrate, ammonium biphosphate, asparagine and protein hydrolyzates, e.g. casein hydrolyzate and whey hydrolyzate. Of the foregoing, urea and ammonium sulfate are preferred.

To optimize yields of organic acids, particularly fumaric acid, available nitrogen in Rhizopus cultures should be limited to a range of about 10 to about 30 mmol available nitrogen per liter medium. Therefore, when urea is employed as a nitrogen source, it is preferred to employ from about 30 to about 90 mg urea per 100 mL of medium.

The inorganic salts added to Rhizopus culture media should include sources of phosphate, sulfur, iron, magnesium and zinc. Suitable sources of phosphate include monobasic or dibasic potassium phosphate, monobasic or dibasic sodium phosphate, ammonium biphosphate or mixtures thereof.

Suitable inorganic salts employed in the fermentation include zinc sulfate, iron salts such as ferric tartrate, and magnesium sulfate.

In a preferred fermentation medium, the carbon source is glucose, the nitrogen source is urea, and potassium dihydrogen phosphate, magnesium sulfate, zinc sulfate, ferric tartrate and corn steep liquor are present.

Suitable esters of fatty acids which can be employed in the process of the invention include esters of aliphatic or microbiologically acceptable cyclic alcohols, e.g. methanol, ethanol, glycerol, glycol, sorbitol, polyols, etc., with fatty acids, saturated or unsaturated, containing about 12 to 24 carbon atoms. Suitable esters include polyoxyethylene sorbitan monolaurate, poloxyethylene sorbitan monopalmitate, polyoxyethylene sorbitan monostearate, polyoxyethylene sorbitan monooleate; triglycerides of lauric, myristic, palmitic, stearic, arachidic, oleic, linoleic, pentadecanoic, linolenic, ricinoleic, palmitoleic, arachidonic acid, methyl laurate, ethyl stearate, ethylene glycol dipalmitate; and sorbitol esters of lauric, myristic, palmitic, and stearic acids. Suitable triglyceride mixtures include corn oil, soybean oil, cottonseed oil, coconut oil, palm oil, olive oil, peanut oil, safflower oil, and sunflower oil.

Preferred are esters derived from fatty acids which contain 16 to 18 carbon atoms, both saturated and unsaturated; corn oil is a preferred triglyceride mixture.

Addition of a fatty acid ester or triglyceride mixture to Rhizopus fermentation media provides significant increases in the rates of production of organic acids. To obtain the benefits of the invention, the amount of fatty acid ester added should be about 200 to about 1000 µg/mL, preferably about 400 to 600 µg/mL.

Process Conditions

Fermentation is with aeration, at a temperature of about 25° C. to 35° C., preferably about 33° C. to 35° C., and at atmospheric pressure. The process of the invention can be adapted to both batch and continuous culture systems. A major product of the fermentation is usually fumaric acid, although lactic acid, succinic acid, malic acid, and other monocarboxylic and dicarboxylic acids can also be produced.

To optimize production of carboxylic acids by the process of the invention, simple neutralization of the acids produced is necessary. Calcium carbonate, which is added to the medium in excess, can be employed to provide pH control and continuous formation of calcium salts of the various product acids.

The fermentation process is allowed to proceed for a time sufficient to obtain optimum yields of the desired carboxylic acids. Times of about 4 to 6 days are preferred. It should be appreciated that fermentation times are influenced to a significant degree by temperature, concentration and choice of microorganisms, nutrient concentration, and other factors known to those skilled in the art. Production rates and yields in individual experiments can be significantly affected by such unpredictable factors as strain deterioration and adventitious impurities in media formulations and culture equipment. Accordingly, culture conditions should be continuously monitored and the productivity of fungal strains frequently checked.

After the process of this invention has gone to completion, the desired acid can be collected in pure form by conventional methods. Calcium salts of product acids can be converted to free carboxylic acids by acidification with mineral acid. Fungal mycelia and insoluble $CaSO_4$ can be removed by heating media to 80° C. to 100° C. for a brief period, followed by filtration. The resulting product acids can be recovered by crystallization.

The concentration of the microorganism required to efficiently practice the process of the invention is preferably about 3 to 8 percent based on the volume of the reaction medium. Too little microorganism will cause a decrease in fermentation rate, and too large a quantity of microorganism will not improve fermentation rates.

The pH of the process medium is determined by the presence of excess calcium carbonate or other neutralizing agent. Generally, the pH of cultures grown in accordance with the process of the present invention should be maintained from about 5 to about 8, preferably from about 5 to about 7.

The following examples illustrate embodiments of the present invention. In the examples, all parts and percentages are by weight, and all temperatures are in degrees Celsius unless otherwise noted.

GENERAL METHODS

Culture Maintenance

*Rhizopus arrhizus* NRRL 1526, *Rhizopus arrhizus* NRRL 2582, *Rhizopus oryzae* ATCC 9363, and *Rhizopus oryzae* ATCC 12732 were preserved by adding 1 mL of spore suspension to 16×150 mm test tubes, each containing 5 g of sterile silica gel (6–16 mesh), agitating the mixture, and incubating the spore-silica suspension at 32° for 2 days. After drying, spores were stored at 4°.

Culture Media

The culture media used in the Examples were adapted from those previously described by Rhodes et al., *Appl. Microbiol.* 7:74 (1959), and are set forth in Table 1, below. All media were sterilized by autoclaving. Medium A, below, was used in Rhizopus spore development. Medium B was employed for Rhizopus vegetative seed germination, and Medium C was used for production of organic acids in aerobic fermentation experiments. Urea was sterilized separately from other media components by autoclaving, and added aseptically to media mixtures prior to inoculation.

TABLE 1

| Ingredient (g/L) | Culture Media | | |
|---|---|---|---|
| | A Sporulation | B Germination | C Production |
| Glucose | 4.0 | 15.0 | 100 |
| Molasses | — | 10.0 | — |
| Lactose | 6.0 | — | — |
| Glycerol | 10.0 (mL) | — | — |
| Urea | 0.6 | 1.0 | 0.6 |
| Peptone | 1.6 | — | — |
| Corn steep liquor | 1.0 (mL) | 3.0 (mL) | 0.5 (mL) |
| $KH_2PO_4$ | 0.4 | 0.3 | 0.3 |
| $MgSO_4.7H_2O$ | 0.3 | 0.25 | 0.4 |
| $ZnSO_4.7H_2O$ | 0.088 | 0.066 | 0.044 |
| Ferric tartrate | — | 0.01 | 0.01 |
| $FeSO_4.7H_2O$ | 0.25 | — | — |

TABLE 1-continued

| Ingredient (g/L) | Culture Media | | |
|---|---|---|---|
| | A Sporulation | B Germination | C Production |
| CuSO$_4$ | 0.005 | — | — |
| MnSO$_4$.4H$_2$O | 0.05 | — | — |
| KCl | 0.4 | — | — |
| NaCl | 40.0 | — | — |
| Agar | 30.0 | — | — |
| Corn Starch | — | 30.0 | — |
| CaCO$_3$ | — | — | 100.0 |

Preparation of Inoculum

Working spore slants were prepared by adding 5 mL of sterile 0.05M phosphate buffer, pH 6.8, containing 0.1% of polyethylene sorbitan monooleate, to a dried spore-silica gel mixture and shaking well. One mL of the resulting spore suspension was plated on a Medium A agar slant which was incubated at 32° for 5-7 days.

Vegetative mycelial seed cultures were prepared by resuspending spores from 5-7 day Medium A agar slants in 30 mL of 0.05M phosphate buffer, pH 6.8, containing 0.1% of polyoxyethylene sorbitan monooleate. The resulting spore suspensions were transferred to 500 mL baffled Erlenmeyer flasks containing 90 mL of sterile Medium B, and incubated with agitation at 32° for 18-24 hours. The resulting cell growth is referred to as "standard inoculum".

Fatty Acid Esters

The fatty acid esters employed in the Examples were as follows: Ester A, polyoxyethylene sorbitan monolaurate (Tween 20 ®); Ester B, polyoxyethylene sorbitan monopalmitate (Tween 40 ®); Ester C, polyoxyethylene sorbitan monostearate (Tween 60 ®); Ester D, polyoxyethylene sorbitan monooleate (Tween 80 ®).

Analysis

Dicarboxylic acids were extracted by adding 10 mL of 6N sulfuric acid to each flask, heating to 80°, and separating the resulting suspension by filtration. Filtrates were analyzed for dicarboxylic acids by high performance liquid chromatography using a Du Pont Instruments 850 liquid chromatograph, temperature controlled column compartment, ultraviolet spectrophotometer, and an auto injector set for 100 ul injections at 7-10 min. intervals with a 30-second flush time. Detection was at 215 nm. An amine-modified silica chromatographic column (4.6 mm×25 cm), prepared by reaction of 5-6 μm completely porous silica particles with 3-aminopropyltriethoxysilane, was used at 50° and at a flow rate of 2 ml/min. The mobile phase consisted of 90% water, acidified to pH 2 with phosphoric acid, and 10% methanol.

Glucose concentrations were determined colorimetrically, using a commercial test kit (Sigma ®) incorporating hexokinase and glucose-6-phosphate dehydrogenase. The test method employed was substantially similar to that described by Carroll, et al., *Biochem. Med.* 4:171 (1970). Molar yields of fumaric acid were calculated on the basis of glucose consumed during fermentation.

EXAMPLES 1-2

Erlenmeyer flasks (250 mL), each of which contained 5 g of calcium carbonate, were sterilized by heating at 160° for 24 hours. 50 mL of Medium C, containing 100 g/L of D-glucose, were added to each flask. Each flask was inoculated with 4% (V/V) of a standard inoculum of *Rhizopus arrhizus* NRRL 1526, 300 μg/mL of Ester B and 300 μg/mL of Ester D were added, and the flasks were incubated for either 2 days (Example 1) or 4 days (Example 2) at 32° in a gyratory shaker. Control experiments were conducted without added fatty acid esters. The results are summarized in Tables 2 and 3, below.

TABLE 2

| | Two Day Incubation | | |
|---|---|---|---|
| Example | Fumaric Acid (g/L) | Succinic Acid (g/L) | Malic Acid (g/L) |
| 1 | 38.8 | 0.2 | 5.3 |
| Control | 23.4 | 1.0 | 4.9 |

TABLE 3

| | Four Day Incubation | | |
|---|---|---|---|
| Example | Fumaric Acid (g/L) | Succinic Acid (g/L) | Malic Acid (g/L) |
| 2 | 50.4 | 3.1 | 9.4 |
| Control | 43.1 | 2.3 | 10.4 |

The results indicate that addition of fatty acid esters increased the fumaric acid yield by 66% and 17% after 2 days and 4 days incubation, respectively, compared with the controls.

EXAMPLES 3-6

The procedure of Example 1 with *Rhizopus arrhizus* NRRL 1526 was substantially repeated except that the concentrations and types of fatty acid esters employed were varied as shown. The results are summarized in Table 4.

TABLE 4

| Example | Fatty Acid Ester | Concentration (μg/mL) | Glucose Consumed (g/L) | Fumaric Acid | |
|---|---|---|---|---|---|
| | | | | Produced (g/L) | Molar Yield % |
| 2 Day Incubation | | | | | |
| 3A | A | 600 | 43 | 17.0 | 61.1 |
| 4A | B | 600 | 44 | 14.8 | 52.0 |
| 5A | C | 600 | 49.5 | 31.6 | 98.9 |
| 6A | D | 600 | 47.5 | 15.1 | 49.2 |
| Control A | — | — | 45.0 | 13.5 | 46.4 |
| 4 Day Incubation | | | | | |
| 3B | A | 600 | 81 | 28.3 | 54.2 |
| 4B | B | 600 | 89 | 28.5 | 47.0 |
| 5B | C | 600 | 92 | 39.7 | 67.0 |
| 6B | D | 600 | 88 | 32.5 | 57.4 |
| Control B | — | — | 82.5 | 27.6 | 51.9 |

These results show that addition of fatty acid esters increased fumaric acid yields by 10% to 134% after 2 days incubation, and by 3% to 44% after 4 days incubation, compared with the controls.

EXAMPLES 7-11

The procedure of Example 1 with *Rhizopus arrhizus* NRRL 1526 was substantially repeated except that various mixtures of Esters B and D were evaluated as indicated. The results are summarized in Table 5.

TABLE 5

| Example | Fatty Acid Ester | Concentration (μ/mL) | Glucose Consumed (g/L) | Fumaric Acid Produced (g/L) | Molar Yield % |
|---|---|---|---|---|---|
| 2 Day Incubation | | | | | |
| 7A | B | 600 | 71.5 | 31.1 | 67.5 |
| 8A | D | 600 | 76.5 | 33.5 | 67.7 |
| 9A | B | 300 | 78 | 36.7 | 73.7 |
|    | D | 300 | | | |
| 10A | B | 100 | 73 | 33.2 | 70.6 |
|     | D | 500 | | | |
| 11A | B | 500 | 67.5 | 28.3 | 65.1 |
|     | D | 100 | | | |
| Control A | None | | 75 | 28.4 | 58.6 |
| 4 Day Incubation | | | | | |
| 7B | B | 600 | 106 | 63.6 | 93.2 |
| 8B | D | 600 | 103 | 60.3 | 90.7 |
| 9B | B | 300 | 106 | 63.2 | 92.7 |
|    | D | 300 | | | |
| 10B | B | 100 | 106 | 64.2 | 94.0 |
|     | D | 500 | | | |
| 11B | B | 500 | 97 | 51.8 | 82.9 |
|     | D | 100 | | | |
| Control B | None | | 105 | 54.2 | 80.1 |

The results indicate that, with the exception of Example 11, addition of fatty acid esters increased fumaric acid yields by 10% to 29% after 2 days incubation, and by 11% to 18% after 4 days incubation, compared with the controls.

EXAMPLES 12-14

The procedure of Example 1 was substantially repeated, except that fatty acid esters B and D were replaced with the triglyceride mixtures indicated. The results are summarized in Table 6, below.

TABLE 6

| Example | Triglyceride Mixture | Conc. (μg/mL) | Glucose Consumed (g/L) | Fumaric Acid Produced (g/L) | Molar Yield % |
|---|---|---|---|---|---|
| 2 Day Incubation | | | | | |
| 12A | Corn oil | 500 | 59 | 32.3 | 84.8 |
| 13A | Soybean oil | 500 | 68 | 27.7 | 63.2 |
| 14A | Cottonseed oil | 1000 | 78 | 32.7 | 65.1 |
| Control A | None | | 65 | 30.3 | 71.7 |
| 4 Day Incubation | | | | | |
| 12B | Corn oil | 500 | 89 | 55.4 | 96.6 |
| 13B | Soybean oil | 500 | 93 | 56.4 | 94.0 |
| 14B | Cottonseed oil | 1000 | 93 | 59.6 | 99.4 |
| Control B | None | | 90 | 43.0 | 74.1 |

The results show that adding triglyceride mixtures in the form of natural oils increased fumaric acid production from 29% to 39% after 4 days incubation.

EXAMPLES 15-19

The procedure of Example 1 was substantially repeated except that fatty acid esters B and D were replaced with various concentrations of corn oil as shown. The results are summarized in Table 7.

TABLE 7

| Example | Corn Oil Concentration (μg/mL) | Glucose Consumed (g/L) | Fumaric Acid Produced (g/L) | Molar Yield % |
|---|---|---|---|---|
| 4 Day Incubation | | | | |
| 15 | 50 | 100 | 46.6 | 72.4 |
| 16 | 200 | 100 | 50.0 | 77.7 |
| 17 | 400 | 100 | 56.3 | 87.4 |
| 18 | 600 | 97 | 54.5 | 87.2 |
| 19 | 1000 | 100 | 45.3 | 70.4 |
| Control | 0 | 100 | 45.6 | 70.8 |

The results indicate that optimal increases in fumaric acid yield were obtained in experiments in which 400 to 600 μg/mL of corn oil were added.

EXAMPLE 20

The procedure of Example 1 with *Rhizopus arrhizus* NRRL 1526 was repeated with the following modifications:
(1) D-glucose was replaced with 50 g/L of corn starch;
(2) Fatty acid esters B and D were replaced with 500 μg/mL of corn oil.

The corn starch was added to the calcium carbonate, and the mixture sterilized by dry heating at 160° for 24 hrs.

The results obtained after fermentation were compared with a control composition which did not contain added corn oil. The results are summarized in Table 8.

TABLE 8

| | Fumaric Acid (g/L) | |
|---|---|---|
| Example | Two Day Incubation | Four Day Incubation |
| 20 | 21.5 | 40.5 |
| Control | 19.2 | 32.3 |

The results indicate that a significant increase in the rate of fumaric acid formation is obtained in the presence of added corn oil when corn starch is used as a carbon source.

EXAMPLES 21-22

The procedure of Example 1 was substantially repeated with the following modifications:
(1) *Rhizopus arrhizus* NRRL 1526 was replaced with the fungal strain designated;
(2) Fatty acid esters B and D were replaced with 500 μg/mL of corn oil.

The results obtained were compared with a control composition which did not contain added corn oil. The results are summarized in Table 9.

TABLE 9

| | | Fumaric Acid (g/L) | |
|---|---|---|---|
| Example | Fungal Strain | Two Day Incubation | Four Day Incubation |
| 21 | *Rhizopus arrhizus* NRRL 2582 | 15.6 | 36.7 |
| Control | *Rhizopus arrhizus* NRRL 2582 | 12.7 | 25.5 |
| 22 | *Rhizopus oryzae* ATCC 12732 | 31.0 | 61.4 |
| Control | *Rhizopus oryzae* ATCC 12732 | 32.3 | 56.3 |

The results show that an increase in the rate of fumaric acid formation is obtained in the presence of added corn oil with the alternate fungal strains.

EXAMPLE 23

The procedure of Example 1 was substantially repeated with the following modifications:
(1) *Rhizopus arrhizus* NRRL 1526 was replaced with *Rhizopus oryzae* ATCC 9363;
(2) Fatty acid esters B and D were replaced with 500 μg/mL of corn oil.

*Rhizopus oryzae* ATCC 9363 is a producer of lactic acid as well as fumaric acid (Pritchard, *J. Gen. Microbiol.* 78:125–137 (1973)). The results obtained were compared with a control composition which did not contain added corn oil. The results are summarized in Table 10.

TABLE 10

| | Fumaric Acid (g/L) | | Lactic Acid (g/L) | |
| --- | --- | --- | --- | --- |
| Example | Two Day Incubation | Four Day Incubation | Two Day Incubation | Four Day Incubation |
| 23 | 8.6 | 13.0 | 67.9 | 86.0 |
| Control | 5.6 | 8.8 | 38.0 | 70.0 |

The results show that increases in the rates of formation of both fumaric acid and lactic acid are obtained in the presence of added corn oil.

BEST MODE

The best mode presently contemplated for practicing the invention is demonstrated by Examples 9B and 12B.

We claim:

1. In a process for producing carboxylic acids selected from the group consisting of fumaric acid, succinic acid, malic acid, lactic acid, and mixtures thereof, by growing fungi of genus Rhizopus in a growth medium comprising a carbon source, a nitrogen source, and inorganic salts until said carboxylic acids are formed, the improvement which comprises growing said fungi in the presence of at least one growth medium additive selected from the group consisting of (1) fatty acid esters having fatty acid residues of 12 to 24 carbons, and
(2) triglyceride mixtures wherein the triglyceride mixture is selected from the group consisting of corn oil, soybean oil, cottonseed oil, coconut oil, palm oil, peanut oil, olive oil, safflower oil and sunflower oil, wherein the growth medium additive is present at a concentration effective to increase production and to facilitate excretion of said carboxylic acids.

2. A process according to claim 1 wherein the fungi are *Rhizopus arrhizus*.

3. A process according to claim 2 wherein the growth medium additive is selected from the group consisting of fatty acid esters having fatty acid residues of 16 to 18 carbons and corn oil.

4. A process according to claim 3 wherein the carbon source is glucose.

5. A process according to claim 4 wherein the nitrogen source is urea or ammonium sulfate.

6. A process according to claim 5 wherein the growth medium at inoculation contains about 30 to about 90 mg per 100 mL urea, and about 10 to about 16 g per 100 mL glucose.

7. A process according to claim 6 wherein the inorganic salts include potassium dihydrogen phosphate, magnesium sulfate, zinc sulfate and ferric tartrate, and corn steep liquor is added to the growth medium.

8. A process according to claim 7 wherein the fatty acid esters or corn oil are present in the growth medium at a concentration of about 200 to about 1000 μg per mL.

9. A process according to claim 8 wherein the fatty acid esters or corn oil are present in the growth medium at a concentration of about 400 to about 600 μg per mL.

10. A process according to claim 9, conducted at a temperature of about 33° C. to about 35° C.

11. A process according to claim 10 wherein the growth medium additive is a fatty acid ester having fatty acid residues of 16 to 18 carbons.

12. A process according to claim 10 wherein the growth medium additive is corn oil.

* * * * *